(12) United States Patent
Geiss (10) Patent No.: US 6,593,136 B1
(45) Date of Patent: Jul. 15, 2003

(54) CULTURING CELLS IN A CHAMBER IN A STACK OF CHAMBERS

(75) Inventor: Kevin T. Geiss, Oxford, OH (US)

(73) Assignee: Geo-Centers, Inc., Newton, MA (US)

( * ) Notice: Subject to any disclaimer, the term of this patent is extended or adjusted under 35 U.S.C. 154(b) by 0 days.

(21) Appl. No.: 09/594,815

(22) Filed: Jun. 16, 2000

Related U.S. Application Data (60) Provisional application No. 60/190,086, filed on Mar. 20, 2000.

(51) Int. Cl.[7] .............................. C12N 5/06; C12N 5/08; C12N 1/00; C12Q 1/02; C12M 3/00
(52) U.S. Cl. ........................ 435/325; 435/29; 435/243; 435/363; 435/366; 435/283.1; 435/289.1; 435/294.1; 435/305.1
(58) Field of Search .......................... 435/29, 325, 363, 435/366, 383, 283.1, 289.1, 294.1, 305.1, 243

(56) References Cited

U.S. PATENT DOCUMENTS

| | | | | |
|---|---|---|---|---|
| 3,886,047 A | * | 5/1975 | Billups, Jr. ............... | 435/305.3 |
| 4,833,083 A | * | 5/1989 | Saxena ........................ | 435/403 |
| 4,935,371 A | | 6/1990 | Rickloff ...................... | 435/296 |
| 5,508,174 A | | 4/1996 | DelRaso ..................... | 435/32 |
| 5,908,776 A | | 6/1999 | Burbaum et al. ......... | 435/288.3 |

OTHER PUBLICATIONS

Web page of www.brincubator.com, description of "Hot Box System", "Hypoxia Chamber", and "Modular Incubator Chamber", sold by Billups–Rothenberg, Inc. of Del Mar, CA. Undated.

* cited by examiner

*Primary Examiner*—David M. Naff
(74) *Attorney, Agent, or Firm*—Michael Tobias (57) ABSTRACT

A chamber has a lid that permits opening and closing of the chamber for inserting or removing a cell culture from the chamber while the chamber is in a stack of chambers without removing any of the chambers from the stack. The lid of the chamber may have one or more ports which enable substances to be introduced into or removed from the chamber when the chamber is sealed by the lid. In one embodiment, the lid is a side wall of a rectangular chamber in a stack of rectangular chambers. Spacers may be provided between the chambers of the stack to provide space between the chambers and restrict horizontal movement of the chambers relative to each other. A flexible container containing an atmosphere may be connected to a port of the chamber, and the atmosphere may be transferred to the chamber by compressing the flexible container. After a cell culture is introduced into the chamber, the stack of chambers may be placed into an incubator. The chamber is suitable for exposing a cell culture in the chamber to volatile and potentially hazardous chemicals to test for the effect of the chemicals on the cell culture.

22 Claims, 10 Drawing Sheets

CULTURING CELLS IN A CHAMBER IN A STACK OF CHAMBERS

REFERENCE TO RELATED APPLICATIONS

This application claims the benefit of U.S. Provisional Patent Application No. 60/190,086 filed on Mar. 20, 2000.

BACKGROUND OF THE INVENTION

1. Field of the Invention

The present invention relates generally to an apparatus for chemical testing. More particularly, it relates to a chamber suitable for exposing cell cultures to volatile chemicals or hazardous materials.

2. Description of the Related Art

The use of cell culture systems has gained increased importance in the area of toxicity research. The recent push to reduce or replace test animals with in vitro testing has been a significant driver of this change. In many applications, chemicals that exhibit good potential for industrial or military use may be quite volatile. This poses a problem both in the potential for personnel exposure to possibly hazardous chemicals and in safety testing of such exposure. A major challenge for the in vitro testing of volatile chemicals is that in contrast to an animal system, which uptakes vapor through breathing, cell cultures are "open" and rely on diffusion of chemicals into culture media before the chemicals enter the cells. The volume of the atmosphere in the surrounding chamber generally is much greater than the volume of the culture media or of cells in culturing vessels. Another major challenge arises from the inherent properties of the chemicals. Volatile chemicals are readily lost by diffusion out of cells and culture media into the atmosphere. This poses a problem in assessing the toxicity of such chemicals because as time progresses during an experiment and chemicals are lost, the actual dose to which cells are exposed changes, resulting in a lower and uncontrolled dose over time.

Previous attempts to address these problems have employed plastic bags or plastic containers to create a closed system in which culture vessels can be placed. This approach suffers from a number of disadvantages. For example, the use of plastics in cell culture systems can be disadvantageous, since volatile organic materials are known to absorb (partition) into plastics, thus leading to dosimetry problems and chamber contamination. Furthermore, plastics commonly used for containers react poorly to repeated autoclaving. Also, such closed systems do not allow for the constant regulation of the vital atmosphere (such as the oxygen and carbon dioxide content) with or without chemical additives, or for efficient sampling of the atmosphere within the systems.

SUMMARY OF THE INVENTION

Accordingly, the present invention provides an exposure chamber suitable for use in exposing cell cultures to volatile and potentially hazardous chemicals.

The present invention also provides an exposure chamber that can be made of substantially inert and impermeable materials so at not to react with or absorb chemicals contained therein.

The present invention additionally provides an exposure chamber with sufficient thermal stability to protect the interior of the chamber from temperature changes when the chamber is moved from one room or environment to another, or when substances are added to or removed from the chambers.

The present invention yet further provides an exposure chamber that can be stacked with one or more other chambers, one atop another.

The present invention also provides an exposure chamber which enables objects to be placed into or removed from the exposure chamber while the exposure chamber is disposed in a stack with one or more other exposure chambers.

The present invention additionally provides an exposure chamber which enables chemicals to be introduced into the exposure chamber and enables samples to be removed from the exposure chamber while the chamber is closed.

According to one form of the present invention, an exposure chamber for cell cultures includes a chamber body having an opening through which cell cultures can be introduced and a lid detachably mounted on the opening. When the lid is removed from the opening, cell cultures in culturing vessels can be introduced into or removed from the chamber body. The chamber preferably includes one or more fluid ports through which a fluid, such as an atmosphere to which cell cultures are to be exposed, can be introduced into the chamber when the chamber body is closed by the lid. In preferred embodiments, the chamber body and the lid are made of glass.

In preferred embodiments, the lid is capable of being mounted on and removed from the chamber body with the chamber disposed above or below another chamber in a stack. Preferably, adjoining chambers in a stack can engage with each other to prevent relative horizontal movement of the chambers.

According to another form of the present invention, a method of culturing cells includes placing a cell culture into a chamber, closing the chamber, introducing an atmosphere into the closed chamber via a fluid port of the chamber, and placing the chamber into an incubator. In a preferred embodiment, an atmosphere is introduced into the closed chamber from a bag or other compressible container in which the atmosphere has previously been prepared and which is compressed to force the atmosphere into the chamber. A previously existing atmosphere within the chamber may be displaced by the introduced atmosphere in another compressible container. The interior of the chamber may be sampled through a port of the chamber.

A standard incubator can generally expose the cell cultures therein to only a single atmosphere at one time. In contrast, by using a plurality of exposure chambers according to the present invention disposed in an incubator, the cell cultures in different exposure chambers can be exposed to different atmospheres simultaneously, enabling the incubator to be utilized much more efficiently. Since the atmospheres within the exposure chambers are isolated from the atmosphere surrounding them in the incubator, the atmosphere of the incubator itself does not need to be controlled, permitting a decrease in the operating costs of the incubator.

A standard incubator generally has an internal volume much larger than that required by cell cultures disposed therein, so when the incubator is filled with a special atmosphere, the amount of chemicals or gas required to create the atmosphere may far exceed the volume actually required for culturing. In an exposure chamber according to the present invention, the head space of the exposure chamber (the space between the cell cultures and the upper inner surface of the exposure chamber) can be reduced to the minimum necessary to provide the cell cultures in the chamber the volume of atmosphere they need to survive. Therefore, the volume of gases and chemicals needed to create a desired atmosphere can be greatly decreased.

An exposure chamber according to the present invention also provides a convenient way to transport cell cultures from place to place while isolating the cell cultures from the environment. The exposure chamber can insulate cell cultures inside it against changes in temperature, humidity, or atmospheric content as the cell cultures are transported, and it can protect lab workers against toxic chemicals which may be present in the exposure chamber. The ports on the exposure chamber enable gases and chemicals to be introduced into or removed from the exposure chamber in a highly controlled manner, thereby reducing the risk to lab workers by avoiding contact with the gases or chemicals.

DESCRIPTION OF PREFERRED EMBODIMENTS

FIGS. 1–5 illustrate one embodiment of an exposure chamber 10 according to the present invention. As shown in these drawings the chamber 10 includes a chamber body 20 having a lid 30 which enables the chamber body 20 to be opened and closed to permit cell cultures being studied to be readily inserted into or removed from the chamber body 20. The chamber 10 also includes one or more ports 40–42 which enable substances to be introduced into or removed from the chamber body 20 when the chamber body 20 is sealed by the lid 30.

Figure 1:
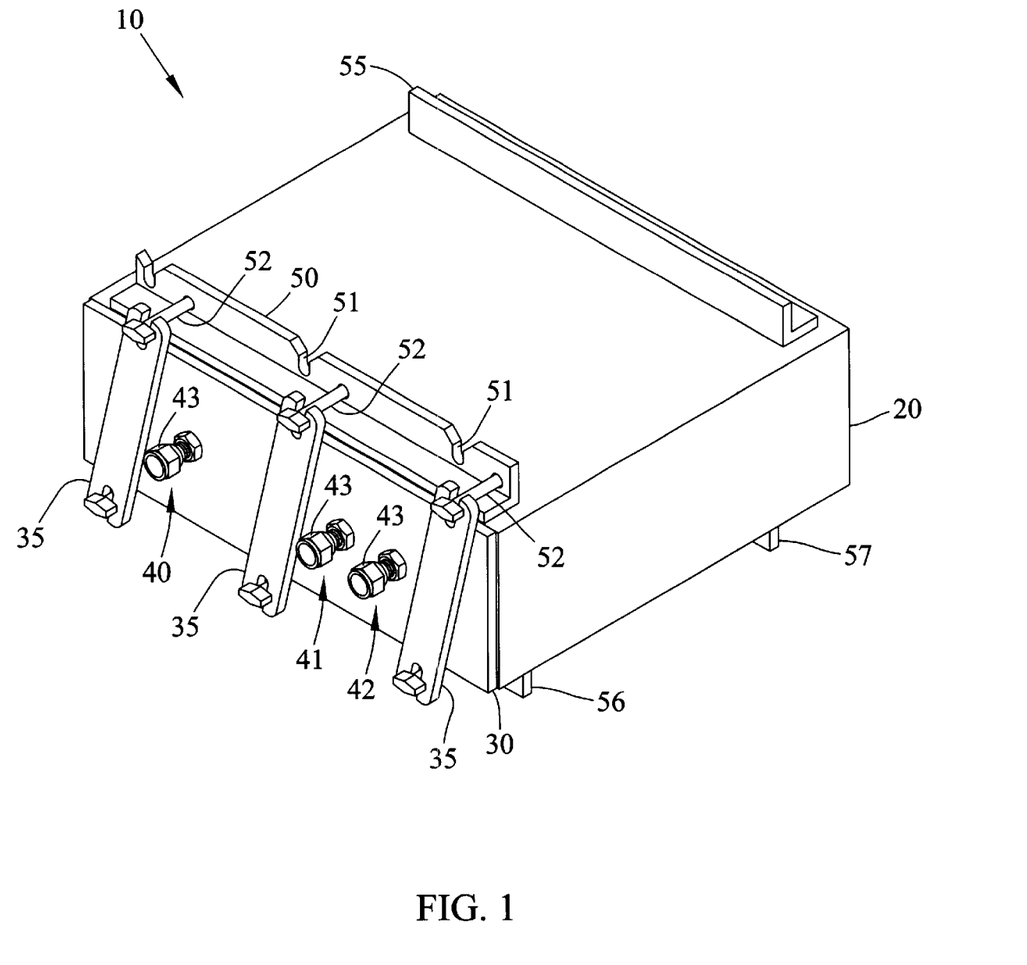
FIG. 1 is an isometric view of an embodiment of an exposure chamber according to the present invention.
Figure 2:
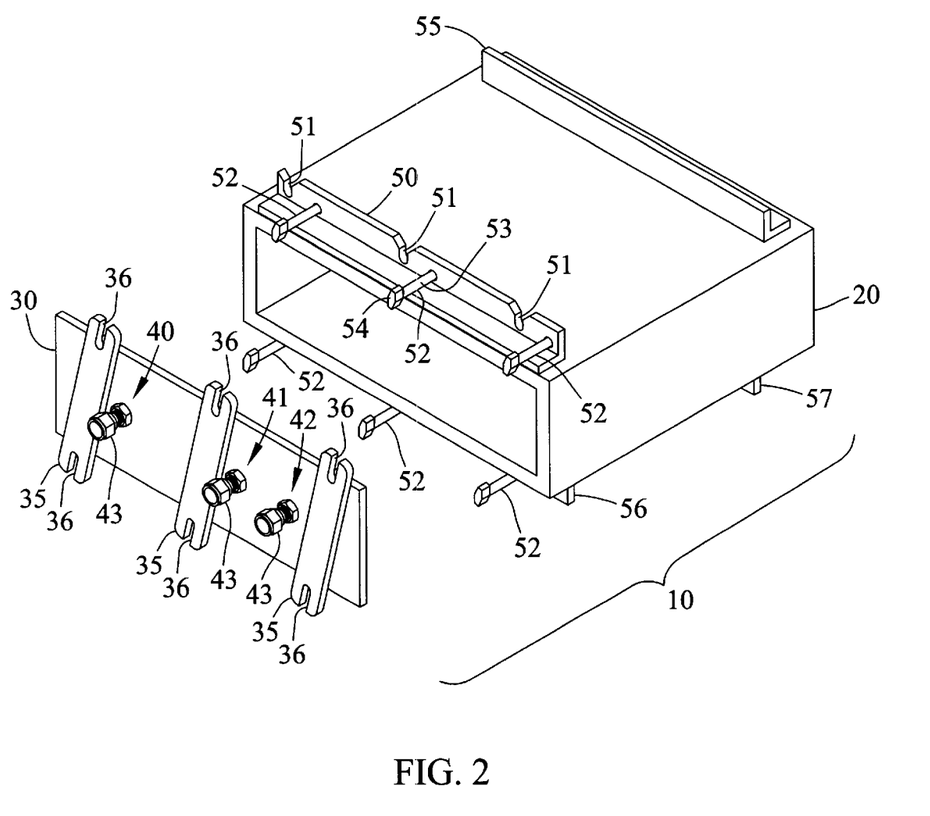
FIG. 2 is an exploded isometric view of the embodiment of FIG. 1.

The chamber body 20 can have any shape which enables it to house a desired number and type of cell cultures. From the standpoint of ease of manufacture, a rectangular body 20 with substantially flat surfaces may be convenient, but a body 20 with curved surfaces or a combination of flat and curved surfaces may also be used. The chamber body 20 and the lid 30 may be made of any material which is compatible with the substances to which it is to be exposed. Materials which are substantially inert, impermeable to fluids, and corrosion resistant are particularly suitable. Glass is a convenient material because it not only has the above-mentioned properties but also because it can be permeable to light to enable the contents of the chamber body 20 to be observed during use. A chamber body 20 and lid 30 made of glass will not absorb substances from an atmosphere contained therein, and they have the ability to be autoclaved numerous times without degradation, enabling them to be reused. However, metals and plastics having the desired properties may also be used. If desired, the chamber body 20 and lid 30 can be formed from commercially available products. For example, the illustrated chamber body 20 and lid 30 are obtained by modifying a glass tank for thin layer chromatography available from Kimble-Kontes of Vineland, N.J.

The volume of the chamber 10 can be selected based on a number of factors, such as the type and the number of cell cultures to be disposed in the chambers 10, the length of time for which culturing is to take place, the culturing conditions, and whether the atmosphere within the chamber 10 is to be renewed during testing. The illustrated chamber body 20 has outside dimensions of roughly 12 inches×10 inches×4 inches and a wall thickness of roughly 0.5 inches. It is particularly advantageous if the chamber 10 is sufficiently small to fit inside a standard lab incubator.

The lid 30 can be mounted on the chamber body 20 in any manner which enables the chamber body 20 to be opened to permit is cell cultures to be inserted or removed, and to be closed to isolate the interior of the chamber body 20 from the atmosphere surrounding the chamber 10. The illustrated lid 30 can be completely detached from the chamber body 20 when the chamber 10 is to be opened, but alternatively, the lid 30 can be attached to the chamber body 20 by a hinge, for example, so as to remain connected to the chamber body 20 when the chamber 10 is open. In the present embodiment, the lid 30 can be detachably secured to the chamber body 20 by a securing mechanism employing screws 52. A plurality of screws 52 (3 in this example) are mounted on an angle iron 50 secured to an top surface of the chamber body 20, and additional screws 52 (3 more in this example) are mounted on an angle iron 56 secured to the bottom surface of the chamber body 20. The shanks 53 of the screws 52 extend parallel to each other towards the front of the chamber body 20. A plurality of bars 35 for engagement with the heads 54 of the screws 52 are secured to the outer surface of the lid 30 so as to extend beyond the upper and lower surfaces of the chamber body 20. Each bar 35 has an opening, such as a slot 36, in each end, with each slot 36 having a width which is large enough for the shank 53 of one of the screws 52 to pass through it. The slits 36 are preferably sufficiently wide to allow the shanks 53 of the screws 52 to freely rotate therein. The head 54 of each screw 52 is shaped so that when rotated to a certain rotational position (such as the position shown in FIG. 2), it can easily pass through the corresponding slot 36 to enable the lid 30 to be removed. However, when the head 54 is rotated to another rotational position (such as the position shown in FIG. 1), it extends beyond the widthwise edges of the slot 36 and thereby prevents the lid 30 from being removed from the chamber body 20. When the head 54 of the screw 52 is in the position shown in FIG. 1, it preferably urges the lid 30 tightly against the front end surface of the chamber body 20. An example of a suitable screw 52 is a quarter-turn screw which can be tightened by a quarter turn between the positions shown in FIGS. 2 and 1.

Screws 52 for securing the lid 30 to the chamber body 20 can be installed in locations other than along the top and bottom surfaces of the chamber body 20. For example, they can be installed on the exterior vertical side walls of the chamber body 20. A securing mechanism employed screws 52 is just one example of means for securing the lid 30 to the chamber body 20, and a wide variety of conventional securing devices, such as those used to fasten luggage, to secure lids to containers, or to close windows or doors, can instead be employed.

Although not always required, it is frequently desirable to be able to seal the lid 30 against the chamber body 20 in a gas-tight manner to isolate the interior of the chamber body 20 from the surrounding atmosphere. A seal may be formed by direct contact between the lid 30 and the chamber body 20, or a sealing member, such as an O-ring, a gasket, or a sealing compound may be sandwiched between the two members to form a seal. In the present embodiment, a gas-tight seal is formed by glass-to-glass contact between the lid 30 and the end surface of the chamber body 20.

In addition to angle irons 50 and 56, the rear of the illustrated chamber body 20 is equipped with an angle iron 55 on its top surface and an angle iron 57 on its bottom surface. Angle iron 55 has the same height as angle iron 50, and angle iron 57 has the same height as angle iron 56. The angle irons 50 and 55–57 function as spacers to separate the top and bottom surfaces of the chamber body 20 from another chamber body 20 disposed above or below it when a plurality of chambers 10 are disposed in a stack, and they also prevent relative horizontal movement of adjoining chambers 10 in a stack. A space formed by the angle irons above or below a chamber body 20 provides clearance to facilitate removal or installation of the lid 30. In addition, spaces above and below a chamber body 20 makes it easier for a user to lift a chamber 10, since the user can obtain a secure grip by inserting his fingers into the spaces.

The ports 40–42 enable substances (such as gases, chemicals, or cells) to be introduced into or removed from the chamber 10 without it being necessary to remove the lid 30 from the chamber body 20. The number of ports is not restricted and can be varied depending upon the intended uses of the ports. Thus, there may be a single port or any larger number of ports. The illustrated embodiment employs first through third ports 40–42, with one of the ports typically being used to introduce a gas atmosphere into the chamber body 20, another of the ports being used to exhaust gas from the chamber body 20, and a third of the ports being used for sampling substances from the interior of the chamber body 20. However, it is possible to reduce the number of ports and to use a single port for more than one purpose.

The ports 40–42 can be formed on any convenient location of either the lid 30 or the chamber body 20. The lid 30 is often a convenient location from the standpoints of ease of installation and ease of access during use of the chamber 10. The ports 40–42 may be equipped with fittings 43 which enable the ports 40–42 to be fluidly connected, either permanently or detachably, with fluids conduits such as hoses, pipes, or tubing, or with syringes or other equipment. In the present embodiment, each port 40–42 comprises an unillustrated hole formed through the thickness of the lid 30, and a standard bulkhead fitting 43 mounted on the hole. Each of the illustrated fittings 43 is a pipe union fitting including a hollow stem 44 extending through the lid 30 and a securing nut 45 detachably mounted on external threads at the outer end of the stem 44. The securing nut 45 can be used to connect rigid tubing to the fitting 43, or if the securing nut 45 is removed, various members such as valves or connectors can be connected to the outer end of the stem 44, either by a friction fit or by being screwed onto the threads of the stem 44.

When the ports 40–42 are not being used to introduce or remove substances from the chamber 10, they may be sealed, if desired, to isolate the interior of the chamber body 20 from the atmosphere. For example, the fittings 43 may be equipped with removable caps by which they can be sealed, or the fittings 43 may be of a self-sealing type which automatically seals when a hose is removed therefrom. Alternatively, an impermeable sheet or membrane may be disposed between the outer end of a stem 44 and the corresponding securing nut 45.

A wide variety of other types of fittings can be employed with the ports 40–42, such as hose barb connectors, Luer connectors, and quick release vacuum fittings.

Figure 3:
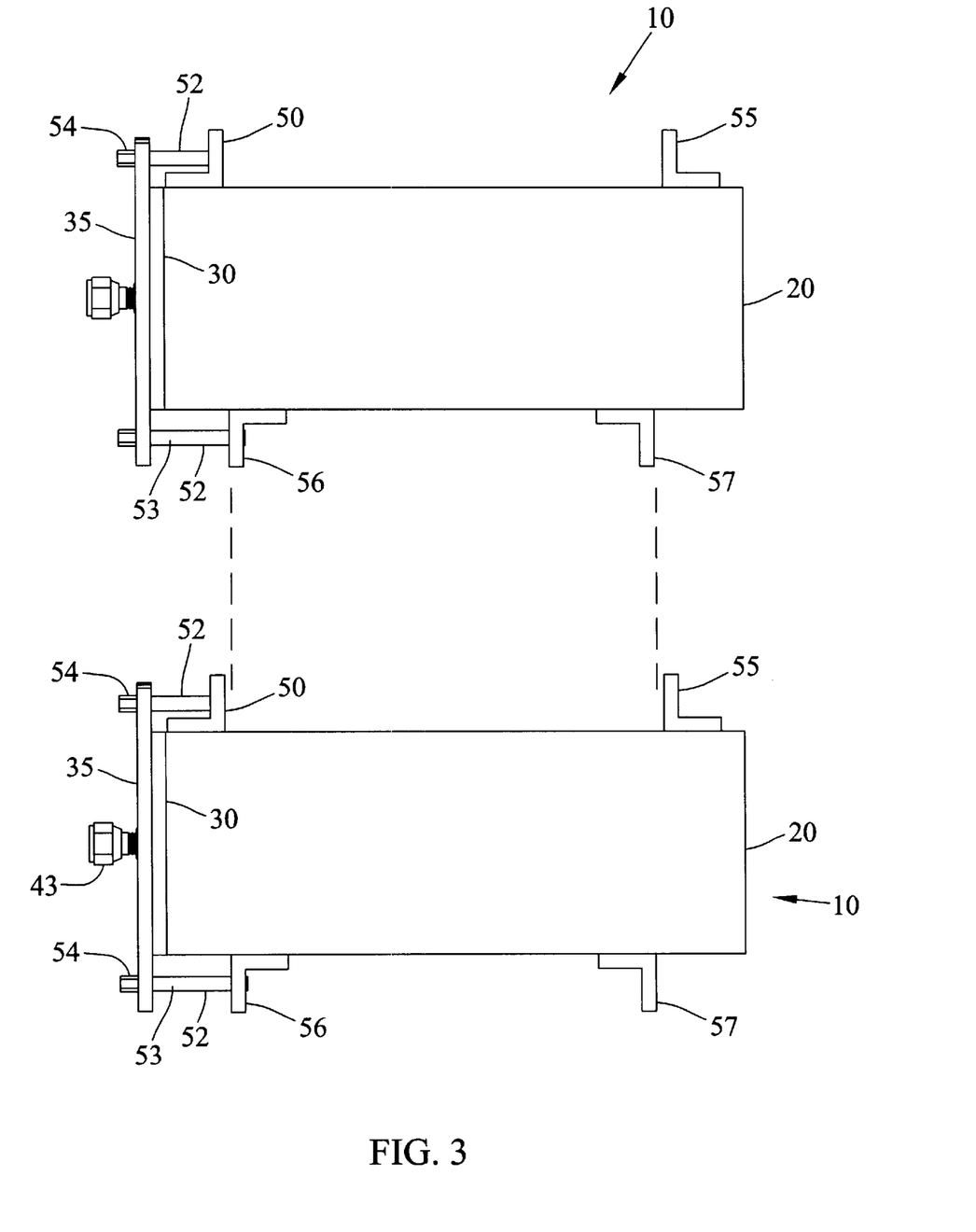
FIG. 3 is a side elevation of two identical exposure chambers like the one of FIG. 1, showing how they can be stacked atop one another.
Figure 4:
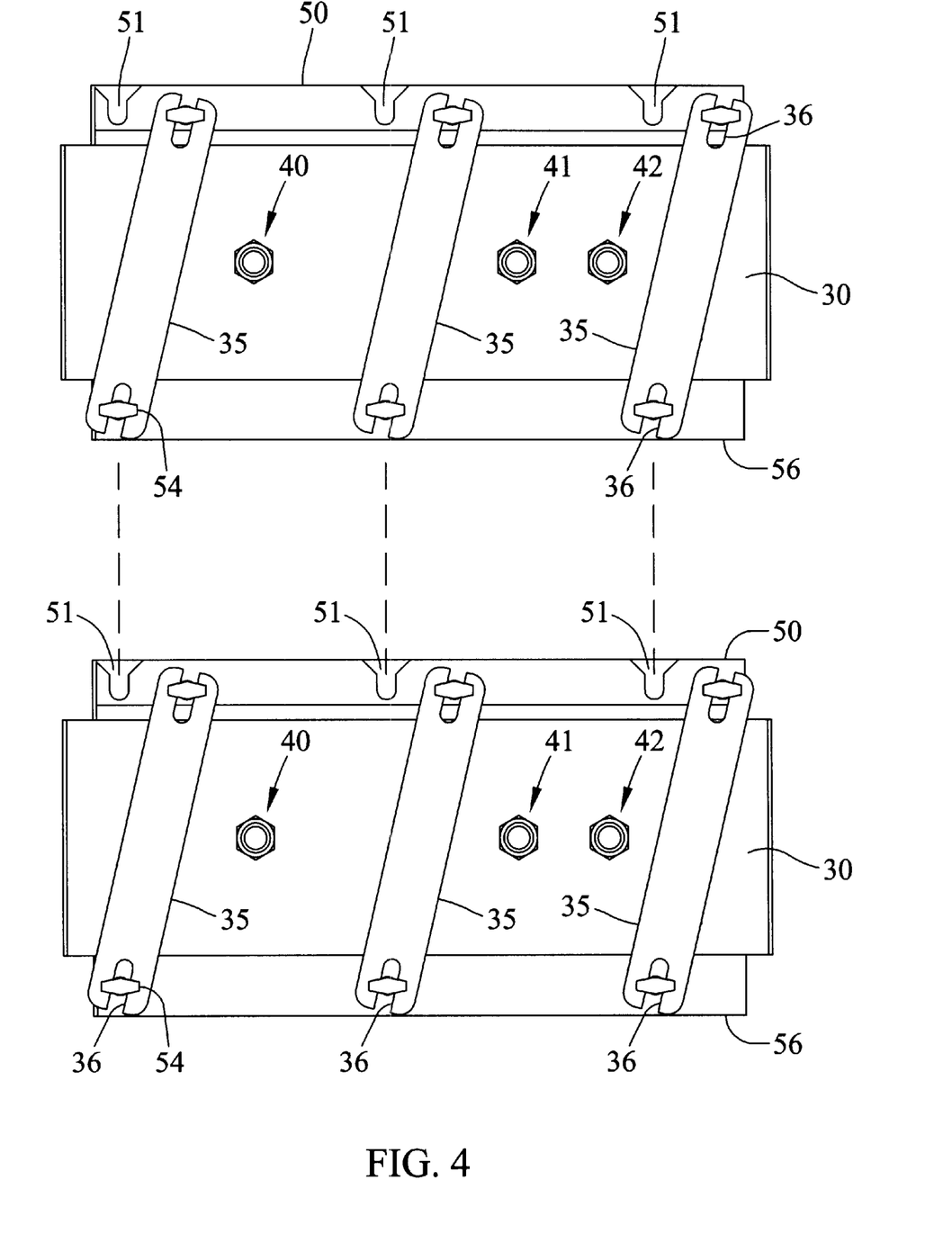
FIG. 4 is a front elevation of the exposure chambers of FIG. 3.
Figure 5:
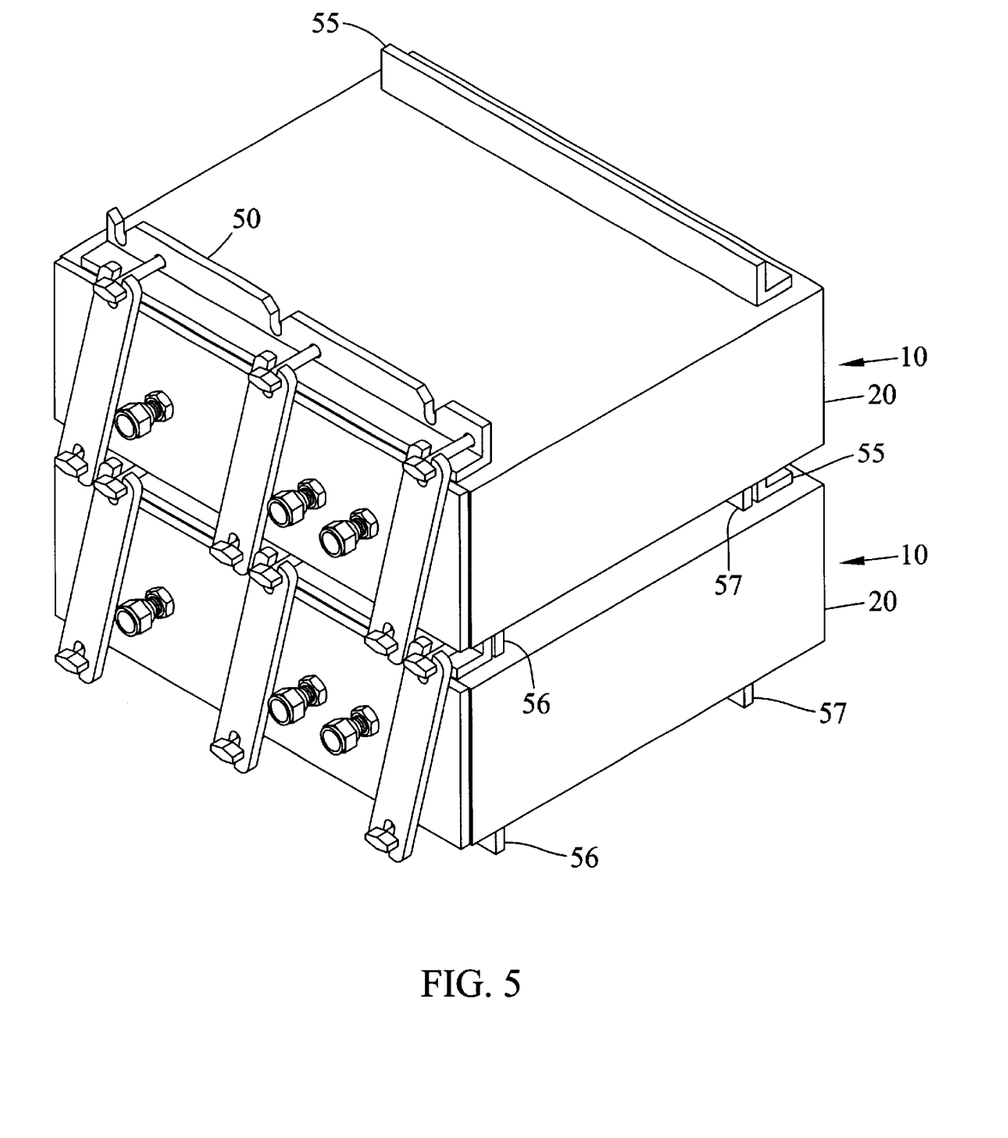
FIG. 5 is an isometric view of the two exposure chambers of FIG. 3 stacked atop each other.

It is convenient if the chamber 10 is constructed such that a plurality of similar chambers 10 can be stacked atop each other, as shown in FIG. 5, for example, while enabling the lid 30 of any chamber 10 in the stack to be mounted and dismounted from the corresponding chamber body 20 without removing the chamber 10 from the stack. As shown in FIG. 3, which is a side elevation of two identical chambers 10 vertically spaced from each other, the maximum distance between the two angle irons 56 and 57 on the bottom of each chamber body 20 is smaller than the distance between the two angle irons 50 and 55 on the top of each chamber body 20 so that the two lower angle irons 56 and 57 can fit between the two upper angle irons 50 and 55 of the chamber 10 below it, thereby restricting relative horizontal movement of the two chambers 10 to the left and right in FIG. 3. As shown in FIG. 4, which is a front elevation of the two chambers 10 of FIG. 3, each of the holes 51 in angle iron 50 is positioned in vertical alignment with the shank 53 of one of the screws 52 at the lower end of the chamber 10 above it. When two chambers 10 are stacked atop each other, the shank 53 of each screw 52 is received in one of the openings 51 in angle iron 50 of the chamber 10 below it. This engagement prevents adjoining chambers 10 from shifting horizontally with respect to each other to the left and right in FIG. 4. Thus, a stable stack of a plurality of chambers 10 can be formed, as shown in FIG. 5. Additional chambers 10 can be stacked atop each other in a similar manner to form a stack of a desired height. The lengths of the bars 35 are such that when the two chambers 10 are stacked atop each other, the bars 35 on the lid 30 of one chamber 10 do not vertically overlap the lid 30 of the chamber 10 above or below it so as not to interfere with removal of the lids 30 from the chambers 10.

The angle irons 50 and 55–57 and the bars 35 can be attached to the chamber body 20 and the lid 30 in any manner suitable for the materials of which they are made. When the angle irons 50 and 55–57 and bars 35 are made of metal and the chamber body 20 and lid 30 are made of glass, bonding is frequently a suitable method, but bolting, molding of the glass around the members to be attached, or other methods commonly used for joining members to glass can be employed. When bonding is used, Loctite Durabond E30CL (an epoxy bonding agent sold by Loctite Corporation of Rocky Hill, Conn.) has been found to provide a particularly good bonding strength.

Figure 6:
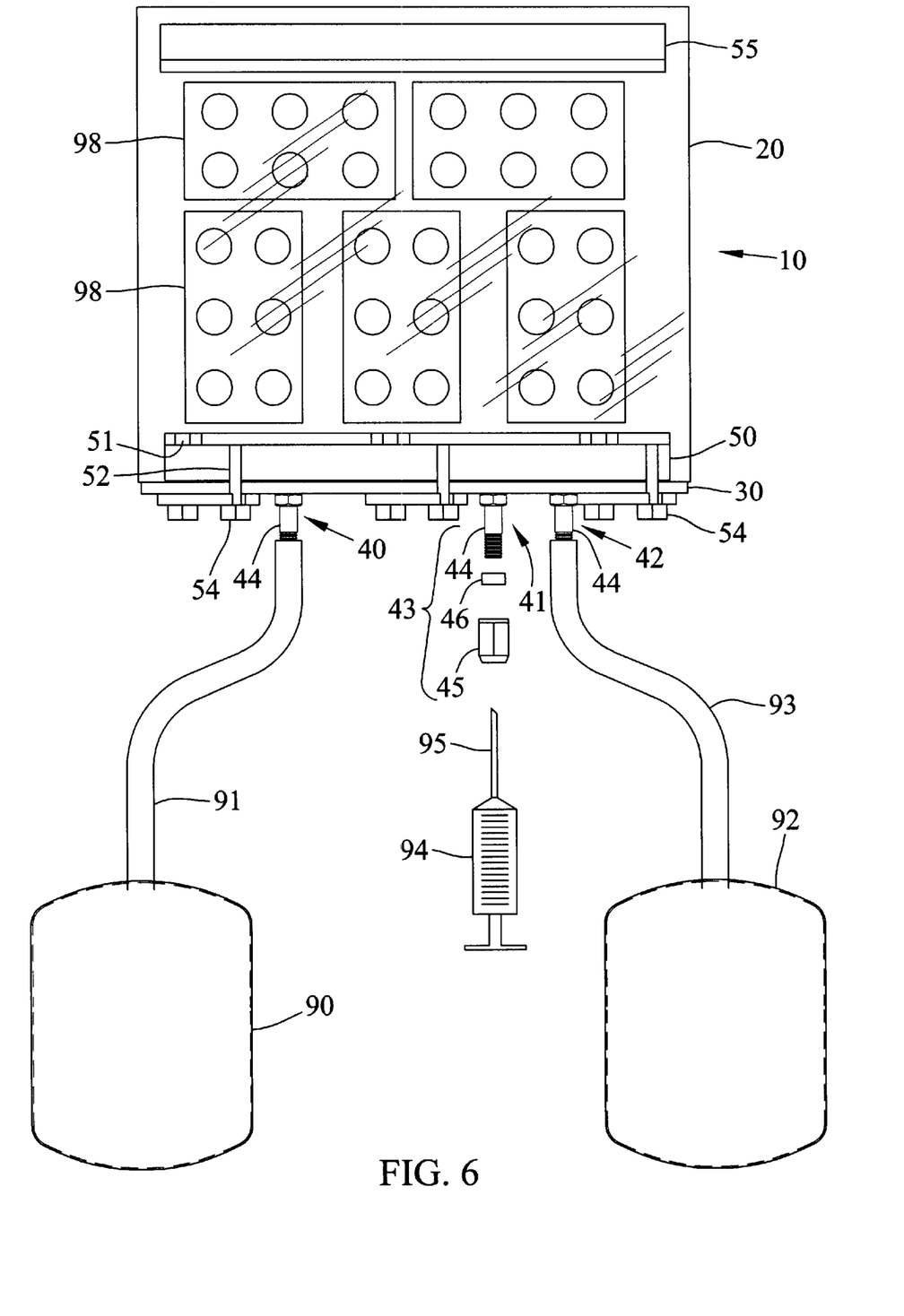
FIG. 6 is a plan view of an experimental setup using the embodiment of FIG. 1.

FIG. 6 schematically illustrates an example of an experimental setup using the embodiment of FIG. 1. The fitting 43 for the first port 40 is connected by a hose 91 to a first bag 90 containing an atmosphere to be introduced into the chamber 10, while the fitting 43 for the third port 42 is connected by a hose 93 to a second bag 92 for receiving gas which is displaced from the chamber 10 by the introduction of the atmosphere from the first bag 90. The bags 90 and 92 can be any bags capable of maintaining an atmosphere therein without leakage or modification of the atmosphere. An example of suitable bag is a commercially available Tedlar bag commonly used for inhalation exposure experiments using lab animals. An elastomeric sheet 46 is placed over the outer end of the threaded stem 44 of the fitting 43 of the second port 41, and is held in place by a nut 45 screwed onto the stem 44. The sheet 46 is capable of being pierced by the needle 95 of a sampling syringe 94 and of resealing itself when the needle 95 is removed. Since the three ports 40–42 of this embodiment are identical in structure, they may be used interchangeably and need not be connected in the manner shown in FIG. 6. The volume of each bag 90 and 92 is at least as great as the volume of the chamber 10 so that the atmosphere within the chamber 10 can be completely displaced by the atmosphere within the first bag 90.

Prior to use, the first bag 90 is filled with an atmosphere having concentrations of $O_2$ and $CO_2$ or other gases, water vapor, and a chemical being studied corresponding to the concentrations which it is desired to maintain in the chamber 10. After cells to be cultured have been placed inside the chamber body 20 on suitable supports (such as on standard multi-well culture plates 98) and the lid 30 has been sealed to the chamber body 20, the first bag 90 is compressed by hand to force the atmosphere from the first bag 90 into the chamber 10. The atmosphere initially in the chamber 10 is displaced therefrom by the atmosphere from the first bag 90 and is discharged via the third port 42 into the second bag 92. After the system is allowed to equilibrate so that the interiors of both bags 90 and 92 and of the chamber 10 are at atmospheric pressure, the first and third ports 40 and 42 are sealed, such as by removing the hoses 91 and 93 from the fittings 43 and replacing them with caps or other members capable of sealing the fittings 43. The chamber 10 can then be placed in an incubator for incubation of the cell cultures. If at any time, such as during incubation, it is desired to sample material within the interior of the chamber 10 (either the atmosphere or the cell cultures), a sampling device such as a needle 95 attached to a syringe 94 can be inserted into the chamber 10 through the elastomeric sheet 46 on the second port 41, and a sample can be withdrawn from the chamber 10 through the needle 95 and into the syringe 94. The elastomeric sheet 46 mounted on the fitting 43 forms a seal against the periphery of the needle 95 passing through it and thus prevents any leakage of the atmosphere from the chamber 10. A gas sample which is withdrawn by the syringe 94 can be supplied to a gas chromatograph, for example, for analysis, while a culture sample which is obtained with the syringe 94 can be submitted to analysis by gas chromatography, high performance liquid chromatography, capillary electrophoresis, or other type of analytical chemical analysis to determine its chemical composition. If it is desired to renew the atmosphere within the chamber 10 during incubation or to replace it with a different type of atmosphere, first and second bags 90 and 92 can again be connected to the fittings 43 for the first and third ports 40 and 42, and an atmosphere can be introduced into the chamber 10 from the first bag 90 while the old atmosphere is discharged into the second bag 92 in the same manner as described above.

At the end of the incubation period, the chamber 10 can be removed from the incubator, and the cell cultures can be removed from the chamber 10 for analysis. Prior to opening the lid 30 of the chamber 10, if the atmosphere in the chamber 10 contains toxic chemicals, it may be desirable to flush the existing atmosphere from the chamber 10 and replace it with a new one which does not pose a danger to lab workers who will be opening the chamber 10. For example, the atmosphere in the chamber 10 can be discharged from the third port 42 and collected in a bag or other container or led to an exhaust hood by a hose to avoid contact with lab workers. An atmosphere can be introduced into the chamber 10 from a container other than a flexible bag, such as from a collapsible bellows-like container, from a piston, or from a vessel containing an atmosphere under pressure.

In a constant flow system, instead of being connected to a bag, the first port 40 can be connected to a source of an atmosphere through a pump, and the third port 42 can be connected to an exhaust hood or reservoir for discharged gas to enable the atmosphere in the chamber to be constantly replaced.

Figure 7:
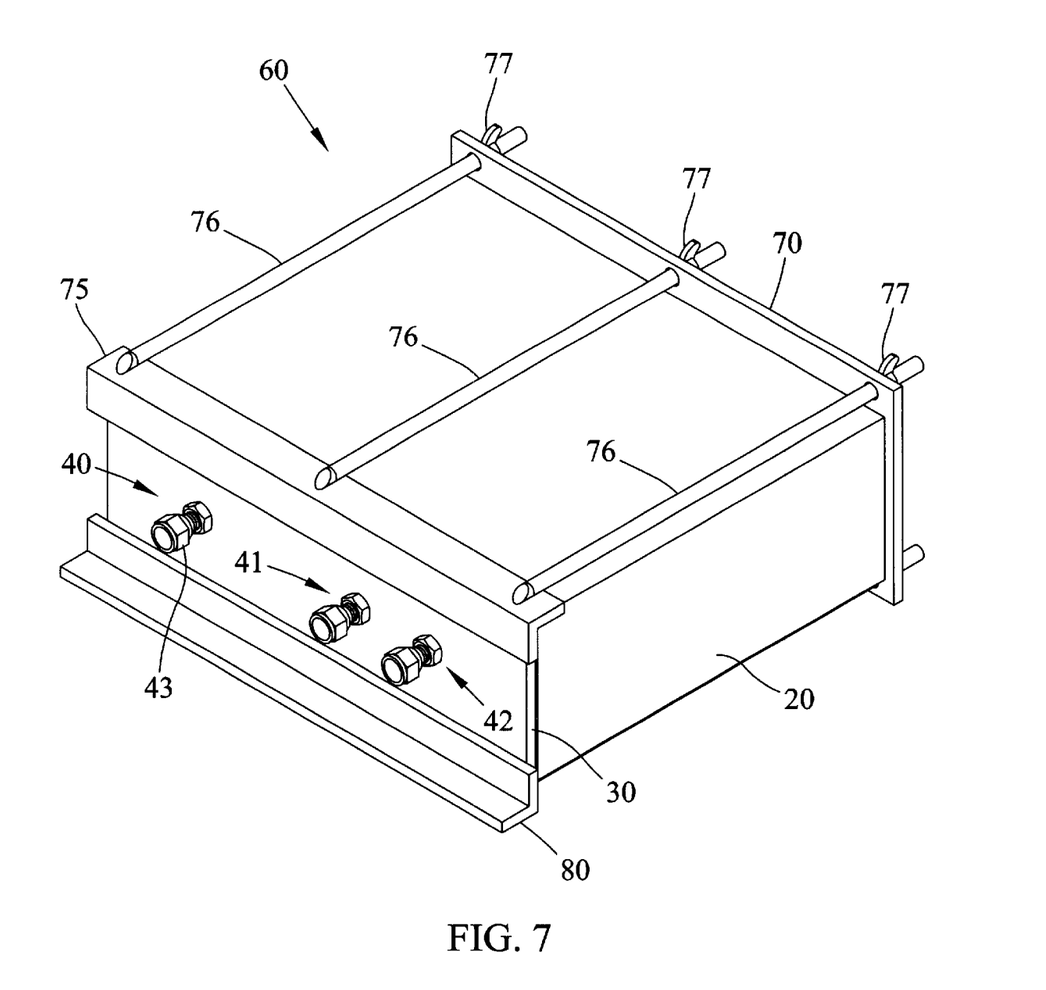
FIG. 7 is an isometric view of another embodiment of an exposure chamber according to the present invention.
Figure 8:
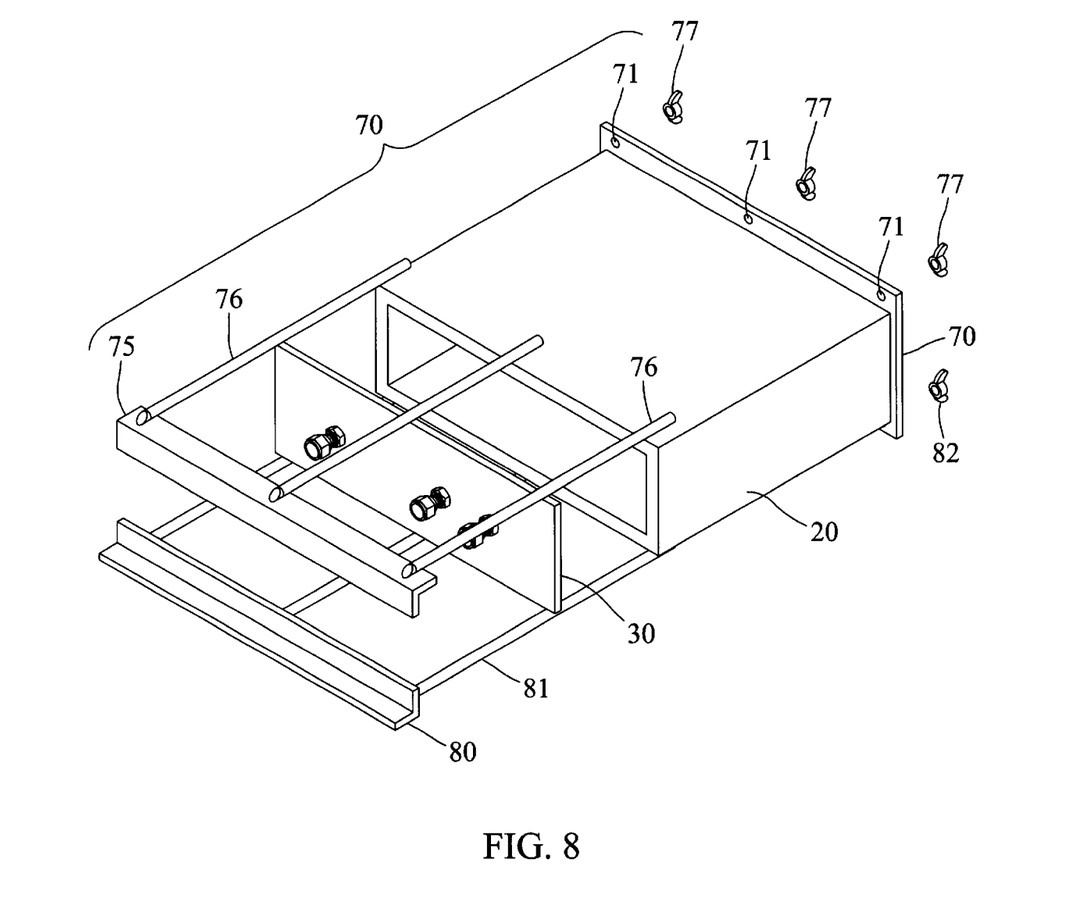
FIG. 8 is an exploded isometric view of the embodiment of FIG. 7.
Figure 9:
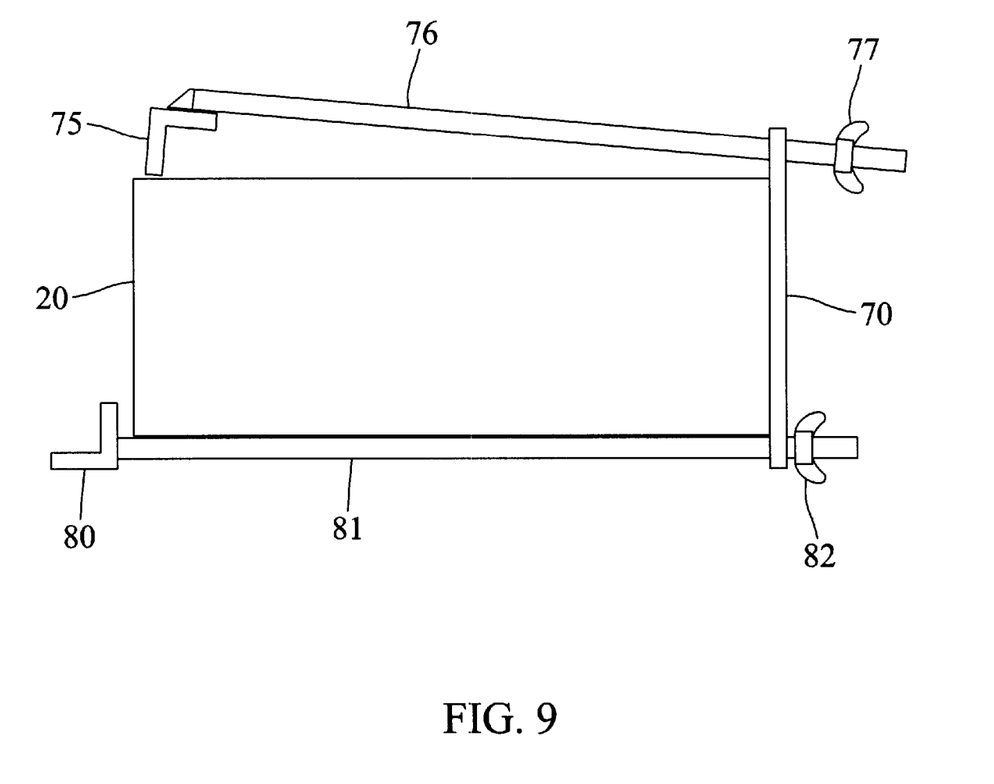
FIG. 9 is a side elevation of the embodiment of FIG. 7 with the lid removed.

FIGS. 7–9 illustrate another embodiment of an exposure chamber 60 according to the present invention which employs a different arrangement for detachably securing a lid 30 to a chamber body 20. FIG. 7 is an isometric view of the exposure chamber 60 in an assembled state, FIG. 8 is an exploded isometric view of the chamber 60, and FIG. 9 is a side elevation of the chamber 60 with the lid removed. This embodiment includes a chamber body 20 and a lid 30, which may be similar in structure to those of the embodiment of FIG. 1. The lid 30 is equipped with a plurality of ports 40–42, which may be similar in structure to the fluid ports of the preceding embodiment. The lid 30 can be detachably secured to the chamber body 20 by a plurality of tie rods 76, 81 extending between a plate 70 at the rear of the chamber body 20 and two angle irons 75 and 80, which can be urged against the lid 30 by the tie rods. The plate 70 may be either secured to or detachable from the chamber body 20. In the present embodiment, the plate 70 is secured to the rear of the chamber body 20 by bonding to enable the chamber body 20 and the plate 70 to be handled as a single unit. The upper angle iron 75 has a vertical leg which overlaps the lid 30 in the vertical direction and a horizontal leg to which a plurality of the tie rods 76 are secured by welding or other suitable method. The lower angle iron 80 has a vertical leg which vertically overlaps the lid 30 vertically and a horizontal leg extending from the vertical leg away from the lid 30. A plurality of tie rods 81 are secured to the lower angle iron 80, such as to the vertical leg thereof. The rear end of each tie rod 76, 81 remote from the angle irons 75, 80 can pass through a corresponding hole 71 in the plate 70 and be immobilized with respect to the plate 70 by a corresponding nut 77, 82 which can be screwed onto it.

One or both of the angle irons 75, 80 may be secured to the lid 30, but in the present embodiment, they are merely pressed by the tie rods against the lid 30 without being connected to it.

In order to open the chamber 60 of FIG. 7, the nuts 77, 82 connected to the rear ends of the tie rods 76, 81 are loosened to permit the angle irons 75, 80 to be moved forward away from the lid 30 by far enough to enable the lid 30 to be removed from the chamber body 20 through the opening at its front end. Once the lid 30 is removed, cell cultures can be placed into or removed from the chamber body 20. At this time, it may be convenient to move one or both of the angle irons 75, 80 away from the opening of the chamber body 20 to permit freer access to the opening. For example, as shown in FIG. 9, the upper angle iron 75 can be temporarily placed atop the upper surface of the chamber body 20. When it is desired to reclose the chamber 60, the lid 30 is placed against the open end of the chamber body 20, the angle irons 75, 80 are positioned so that the lid 30 is disposed between the opening of the chamber body 20 and the vertical legs of the angle irons 75, 80 overlap the lid 30 in the vertical direction, and the nuts 77, 82 on the rear ends of the tie rods 76, 81 are tightened to draw the vertical legs of the angle irons 75, 80 firmly against the lid 30 and press the lid 30 against the chamber body 20 and form a gas-tight seal.

The chamber 60 of FIGS. 7–9 can be used for cell culturing in substantially the same manner as the embodiment of FIG. 1. For example, it can be used in the experimental setup shown in FIG. 6.

A plurality of chambers 60 like the one shown in FIGS. 7–9 can be stacked atop each other to any desired height, with, for example, the plate 70 and the lower angle iron 80 of one chamber 60 resting atop the tie rods 76 of the chamber 60 below it. If the force of one chamber 60 on the tie rods 76 of the chamber 60 below it make it difficult to open the chambers 60 while in a stack, spacers may be provided between adjoining chambers 60 in a stack so that one chamber 60 will not rest on the tie rods 76 of the chamber 60 below it.

The tie rods 76, 81 need not be positioned on the top and bottom sides of the chamber body 20. For example, they can instead be positioned along the vertical side walls of the chamber body 20, thereby making it easier to remove the lid 30 of the chamber 60 when disposed in a stack with other chamber 60. The tie rods 76, 81 need not be permanently secured to the angle irons 75, 80 which restrain the lid 30. For example, the tie rods 76, 81 may pass through holes in the angle irons 75, 80, and be equipped with nuts which can be tightened to press the angle irons 75, 80 against the front surface of the lid 30. In this manner, the tie rods 75, 80 may be loosened and the lid 30 may be removed by loosening nuts on the front of the chamber 60 rather than on the rear thereof.

To test the effectiveness of an exposure chamber according to the present invention, a comparison was made between control cell cultures incubated while simply placed in a standard incubator and test cell cultures incubated while enclosed in an exposure chambers according to the present invention like the one shown in FIG. 7 within a standard incubator. An identical atmosphere (humidified atmosphere at 37° C. containing 95% $O_2$, 5% $CO_2$, and various concentrations of hydrogen peroxide as an example of a nonvolatile chemical) was used for both the control cell cultures and the test cell cultures. The atmosphere within the incubator was maintained by standard techniques, while an atmosphere was introduced into the exposure chambers in the manner described with respect to FIG. 6 after test cell cultures had been sealed inside the chambers. A separate exposure chamber was used for each concentration of hydrogen peroxide. Both the control and test cell cultures were hepatocytes obtained from male Fischer 344 rats in an appropriate medium in 6-well culture plates. After incubation for 4 hours, the viability of the cell cultures was evaluated by a standard MTT assay, in which an MTT (tetrazolium salt) substrate is incubated with the cell cultures. Intracellular reduction of MTT to blue formazan produces a visual indication of cell viability, and the resulting change in optical density is measured spectrophotometrically in a microplate reader at an appropriate wavelength.

Figure 10:
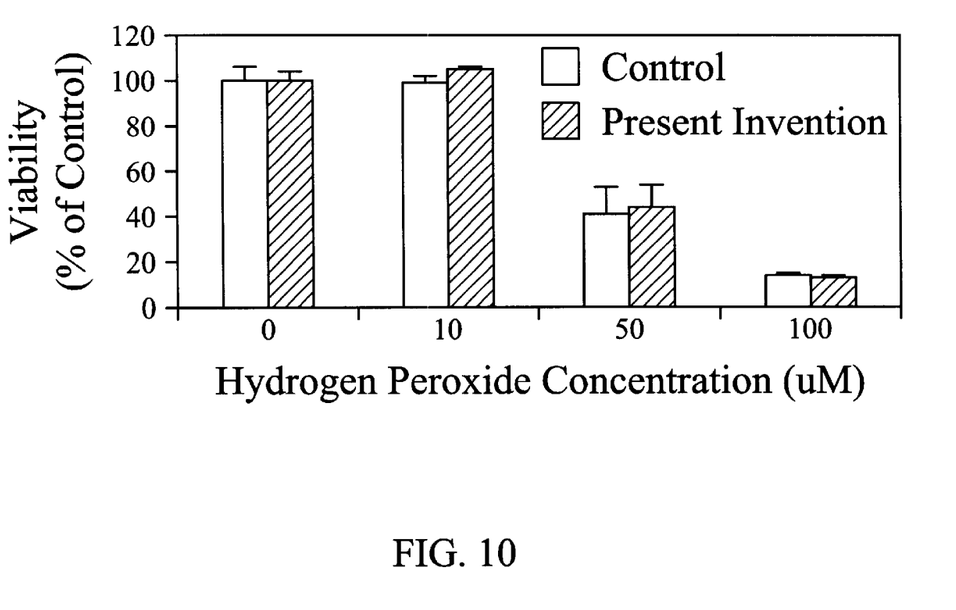
FIG. 10 is a chart illustrating results the results of a toxicology study performed using an exposure chamber according to the present invention.

The results of the assay are illustrated in FIG. 10, in which the viability of cell cultures at each concentration of hydrogen peroxide is expressed as a percentage of the viability of control cells cultured in an atmosphere with no hydrogen peroxide. At no concentration was there a significant difference between the results for the control cell cultures and the test cell cultures, illustrating that an exposure chamber according to the present invention has no effect on cell viability. Thus, the exposure chamber has reliability comparable to that of a standard incubator.

What is claimed is:

1. A method of culturing cells comprising: disposing a first chamber for cell cultures on a second chamber for cell cultures to form a stack;
   removing a lid covering an opening of the second chamber without removing either chamber from the stack by rotating a plurality of screws rotatably supported by a chamber body of the second chamber between a first rotational position in which the screws prevent removal of the lid from the chamber body and a second rotational position in which the screws can pass in a lengthwise direction of the screws through openings formed in rigid members secured to the lid to permit removal of the lid from the chamber body;
   transferring a cell culture between an interior and exterior of the second chamber through the opening in the second chamber; and
   replacing the lid on the second chamber to cover the opening without removing either chamber from the stack.

2. A method as claimed in claim 1, wherein the stack includes a third chamber disposed below the second chamber, and removing and replacing the lid is performed without removing any of the three chambers from the stack.

3. A method as claimed in claim 1, including transferring the cell culture through the opening in a culturing vessel.

4. A method as claimed in claim 1, including placing the cell culture into the chamber in a culturing plate.

5. A method as claimed in claim 1, including engaging a member on a top of the second chamber with screws on a bottom of the first chamber to restrict relative horizontal movement of the first and second chambers.

6. A method as claimed in claim 1, wherein the opening is in a side of the second chamber.

7. A method as claimed in claim 6, wherein the lid defines a side wall of the second chamber.

8. A method as claimed in claim 1, wherein each chamber is rectangular.

9. A method as claimed in claim 1, wherein each chamber has a chamber body and a lid both comprising glass.

10. A method as claimed in claim 1, including forming a gas-tight seal around the opening in the second chamber with the lid.

11. A method as claimed in claim 1, including forming a space between the first chamber and the second chamber with a spacer on a top surface of the second chamber.

12. A method as claimed in claim 1, including forming a space between the first chamber and the second chamber with a spacer on a bottom surface of the first chamber.

13. A method as claimed in claim 1, including forming a space between the first chamber and the second chamber with a spacer on a bottom surface of the first chamber and a spacer on a top surface of the second chamber, the spacers cooperating with each other to restrict horizontal movement of the two chambers relative to each other.

14. A method as claimed in claim 1, including introducing a fluid into the second chamber through a fluid port on the lid of the second chamber.

15. A method as claimed in claim 14, including placing the chambers into an incubator after introducing the fluid.

16. A method as claimed in claim 14, wherein the fluid port includes a fitting for connecting the fluid port to a fluid conduit.

17. A method as claimed in claim 1, including sampling an interior of the second chamber by inserting a needle connected to a syringe through a fluid port on the lid of the second chamber.

18. A method of culturing cells comprising:

disposing a first chamber for cell cultures on a second chamber for cell cultures to form a stack;

removing a lid covering an opening of the second chamber without removing either chamber from the stack;

transferring a cell culture between an interior and exterior of the second chamber through the opening in the second chamber;

replacing the lid on the second chamber to cover the opening without removing either chamber from the stack; and preparing an atmosphere in a flexible container, connecting the flexible container to a fluid port of the second chamber, and compressing the flexible container to introduce the atmosphere from the flexible container into the second chamber.

19. A method as claimed in claim 18, wherein the flexible container comprises a bag.

20. A method as claimed in claim 18, including introducing the atmosphere into the second chamber while displacing a previously existing atmosphere from the second chamber.

21. A method as claimed in claim 20, including collecting the displaced atmosphere in a bag.

22. A method as claimed in claim 18, wherein the atmosphere prepared in the flexible container includes a volatile chemical.

* * * * *